US008070706B2

(12) United States Patent
Gorsuch et al.

(10) Patent No.: US 8,070,706 B2
(45) Date of Patent: *Dec. 6, 2011

(54) APPARATUS AND METHOD FOR IN-VIVO PLASMAPHERESIS USING PERIODIC BACKFLUSH CONTAINING ANTICOAGULANT

(75) Inventors: Reynolds G. Gorsuch, Yountville, CA (US); Tommy Gene Cooper, Friendswood, TX (US); Harold H. Handley, Jr., Encinitas, CA (US); Harold W. Peters, Martinez, CA (US)

(73) Assignee: Transvivo, Inc., Napa, CA (US)

( * ) Notice: Subject to any disclaimer, the term of this patent is extended or adjusted under 35 U.S.C. 154(b) by 424 days.

This patent is subject to a terminal disclaimer.

(21) Appl. No.: 12/353,209

(22) Filed: Jan. 13, 2009

(65) Prior Publication Data
US 2009/0118660 A1 May 7, 2009

Related U.S. Application Data

(63) Continuation of application No. 11/320,866, filed on Dec. 29, 2005, now Pat. No. 7,476,210, which is a continuation-in-part of application No. 10/408,657, filed on Apr. 4, 2003, now abandoned, which is a continuation-in-part of application No. 09/754,773, filed on Jan. 4, 2001, now Pat. No. 6,659,973.

(51) Int. Cl.
*A61M 37/00* (2006.01)
(52) U.S. Cl. ............ 604/6.04; 604/6.09; 604/6.11; 604/4.01; 604/5.01; 604/6.01

(58) Field of Classification Search .......... 604/4.01, 604/5.01, 5.04, 6.04, 6.09, 6.16, 7, 8, 9, 21, 604/27, 28, 264; 422/44; 210/600, 634, 210/644, 645, 646, 500.1, 651, 195.2, 200, 210/203, 500.21, 650, 433.1, 500.23
See application file for complete search history.

(56) References Cited

U.S. PATENT DOCUMENTS

| 4,086,924 A | 5/1978 | Latham, Jr. |
| 4,235,231 A | 11/1980 | Schindler et al. |
| 4,668,214 A | 5/1987 | Reeder |
| 4,708,799 A | 11/1987 | Gerlach et al. |
| 4,832,034 A | 5/1989 | Pizziconi et al. |

(Continued)

FOREIGN PATENT DOCUMENTS
JP 01-094901 4/1989
(Continued)

OTHER PUBLICATIONS

Hofauer, et al., *Effect of Anticoagulation on Blood Membrane Interactions During Hemodialysis*, Kidney International vol. 56 (1999) pp. 1578-1583.

(Continued)

*Primary Examiner* — Leslie Deak
(74) *Attorney, Agent, or Firm* — Knobbe Martens Olson & Bear LLP

(57) ABSTRACT

Method for in-vivo plasmapheresis utilizing a plurality of elongated hollow microporous filter fibers periodically interrupt diffusion of blood plasma from a patient, and, for a selected time, directing backflush fluid into the fibers at a pressure and interval sufficient to cleanse the fiber pores, after which plasma diffusion is resumed. The backflush fluid, preferably a normal saline solution, may contain an anticoagulant such as heparin, citrate or NO donor in suitable concentration for systemic anti-coagulation or for treating the fiber for thromboresistance.

23 Claims, 4 Drawing Sheets

U.S. PATENT DOCUMENTS

| | | | |
|---|---|---|---|
| 4,919,817 A | 4/1990 | Schoendorfer et al. |
| 4,950,224 A | 8/1990 | Gorsuch et al. |
| 5,053,121 A | 10/1991 | Schoendorfer et al. |
| 5,145,583 A | 9/1992 | Angleraud et al. |
| 5,151,082 A | 9/1992 | Gorsuch et al. |
| 5,152,743 A | 10/1992 | Gorsuch et al. |
| 5,211,850 A | 5/1993 | Shettigar et al. |
| 5,224,926 A | 7/1993 | Gorsuch et al. |
| 5,242,382 A | 9/1993 | Gorsuch et al. |
| 5,536,412 A | 7/1996 | Ash |
| 5,549,674 A | 8/1996 | Humes et al. |
| 5,674,452 A | 10/1997 | Carson et al. |
| 5,735,809 A | 4/1998 | Gorsuch et al. |
| 5,868,717 A | 2/1999 | Prost |
| 5,968,004 A | 10/1999 | Gorsuch et al. |
| 5,980,481 A | 11/1999 | Gorsuch et al. |
| 6,044,691 A | 4/2000 | Kenley et al. |
| 6,248,087 B1 | 6/2001 | Spears et al. |
| 6,762,206 B2 | 7/2004 | Khan |
| 6,770,049 B2 | 8/2004 | Ludt et al. |
| 6,802,820 B1 | 10/2004 | Gorsuch et al. |
| 6,802,971 B2 | 10/2004 | Gorsuch et al. |
| 6,849,183 B2 | 2/2005 | Gorsuch et al. |
| 6,899,692 B2 | 5/2005 | Gorsuch et al. |
| 6,946,079 B1 | 9/2005 | Holm |
| 2002/0115559 A1 | 8/2002 | Batchelor et al. |
| 2004/0224868 A1 | 11/2004 | Meyerhoff et al. |
| 2005/0119598 A1 | 6/2005 | Callan et al. |
| 2005/0215936 A1 | 9/2005 | Gorsuch et al. |

FOREIGN PATENT DOCUMENTS

| | | |
|---|---|---|
| JP | 06-170178 | 6/1994 |
| WO | WO99/19007 | 4/1999 |

OTHER PUBLICATIONS

International Search Report for related PCT Application No. PCT/US01/50431 mailed Oct. 9, 2002.

International Written Opinion for related PCT Application No. PCT/US01/50431 mailed Oct. 14, 2002.

Official communication from Japanese Patent Office for related Japanese Patent Application 2002-554159.

Prasad, et al., *Factors Affecting System Clotting in Continuous Renal Replacement Therapy: Results of a Randomized, Controlled Trial*, Clinical Nephrology, vol. 53 (2000), pp. 55-60.

Wang, et al., *Nitric Oxide Donors: Chemical Activities and biological Applications*, Chemical Reviews vol. 102 (2002), No. 4 pp. 1091-1134.

APPARATUS AND METHOD FOR IN-VIVO PLASMAPHERESIS USING PERIODIC BACKFLUSH CONTAINING ANTICOAGULANT

CROSS-REFERENCE TO RELATED APPLICATIONS

This application is a continuation of U.S. patent application Ser. No. 11/320,866 filed Dec. 29, 2005, now U.S. Pat. No. 7,476,210, which is a continuation-in-part of U.S. patent application Ser. No. 10/408,657 filed Apr. 4, 2003, which is a continuation-in-part of U.S. patent application Ser. No. 09/754,773, filed Jan. 4, 2001, now U.S. Pat. No. 6,659,973.

BACKGROUND OF THE INVENTION

In U.S. Pat. Nos. 4,950,224 and 5,151,082, there are disclosed methods and apparatus for carrying out in-vivo plasmapheresis for separating plasma from other blood components within the body and blood vessels of a patient. In the apparatus pumping is used to create a trans-membrane pressure and motivate the flow of fluid from within the in-vivo system, whereby blood plasma is pumped from the patient to a treatment system such as a dialyzer or other apparatus in which toxic metabolic waste in the plasma is removed. After the plasma is treated for removal of waste products, excess fluids, toxins, and/or other deleterious plasma proteins, the treated plasma is returned and reintroduced to the patient's blood stream. Methods of toxin removal from blood using plasma, or portions of the plasma, as taught by the aforesaid patents are unique from and substantially superior to conventional hemodialysis as presently practiced for both acute and chronic kidney failure, primarily because removal of whole blood from the patient's vasculature is eliminated. The methods and apparatus described in the aforesaid patents are incorporated herein by reference.

In U.S. Pat. Nos. 6,802,820 and 6,802,971, there are disclosed specialized hollow fiber membranes which are superior in biocompatibility, performance and morphology for carrying out in-vivo plasmapheresis. In U.S. Pat. No. 6,899,692 there is disclosed a plasmapheresis filter device and catheter assembly incorporating the aforesaid specialized hollow fiber membranes. In U.S. Pat. No. 6,849,183 and U.S. patent application Ser. No. 11/078,016, filed Mar. 11, 2005 (TRANSVI.011CP1) there are disclosed apparatus and methods for therapeutic apheresis and patient fluid management, respectively, using the aforesaid specialized hollow fiber membranes, filter device and catheter assembly. Such fibers, filter device, catheter assembly, apparatus and methods as disclosed in the aforesaid patents and application are incorporated herein by reference.

In the aforesaid systems, the hollow fiber membranes function as filters, where the primary purpose of said membranes is separation of specific blood or plasma components from whole blood. In such systems, the blood (permeate) flows on the outside of the fiber and the plasma (exudate) is diffused through the fiber membrane to the interior lumen of the hollow fiber. However, as use is continued, performance of the fibers as filters becomes degraded over time. For example, clogging or fouling of the filter occurs on the surface of the filter as the pore void spaces become more occluded with particulate matter from the permeate building up within the pore void such that the minute volume of the exudate is progressively degraded to the point of failure and cessation of exudate flow. Such clogging or fouling of the filter membranes, as well as clotting problems with filter systems such as disclosed in the aforesaid patents causes major operational and economic problems with current ex-vivo systems performing Continuous Renal Replacement Therapy (CRRT) for acute and chronic kidney failure. It is reported by Ramesh, Prasad, et al., in *Clinical Nephrology*, Vol. 53, p. 55-60 (January 2000), that over 50% of such filters fail in 10 hours and over 75% fail in 30 hours of usage. Because short-term filter replacement is both undesirable and unacceptable, clogging or fouling failure of filters used in in-vivo systems described in the aforesaid patents would be totally unacceptable for both medical and economic reasons.

SUMMARY OF THE INVENTION

According to the method described herein, in-vivo plasmapheresis is periodically interrupted and a backflush fluid is directed into the interior of the hollow fibers of an implanted filter device for a duration and at a flow rate sufficient to substantially clear the pores of the filter. After a sufficient duration, the backflush is terminated and the plasmapheresis extraction is resumed. The apparatus for carrying out the method includes a filter device comprising the fibers and a multiple lumen catheter secured to the implanted filter device having a first lumen for directing backflush fluid into the hollow fibers, a second fluid for directing plasma from the filter assembly, and a third lumen for returning treated plasma to the patient. The apparatus also includes one or more pumps for pumping the backflush fluid into the filter assembly. In one embodiment of the method the backflush fluid contains an anticoagulant or antithrombotic agent. In another embodiment the backflush fluid contains one or more patient treatment medications.

DETAILED DESCRIPTION OF THE PREFERRED EMBODIMENT

Figure 1:
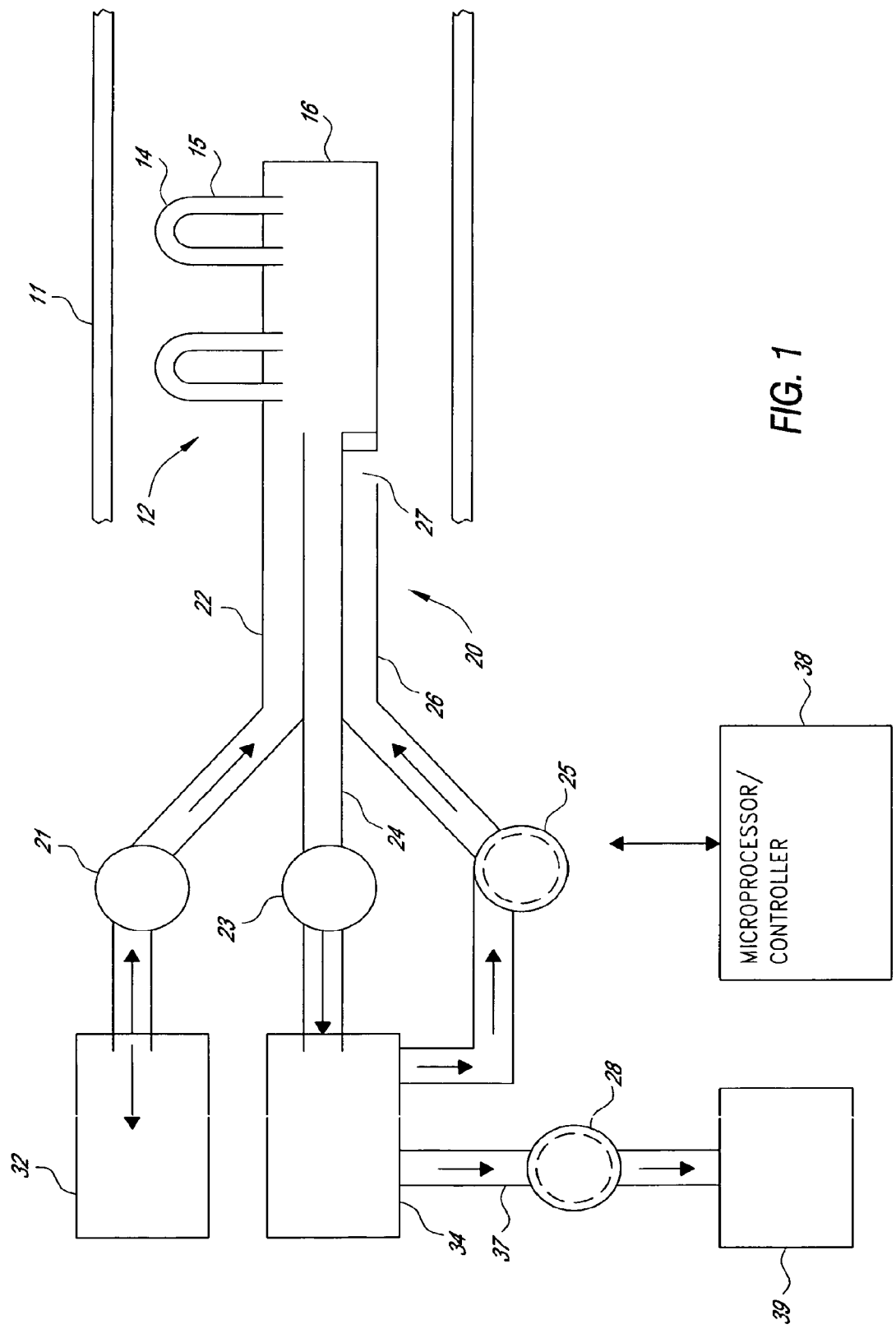
FIG. 1 is a schematic illustration of an apparatus for carrying out the improved method of the invention.

As illustrated in FIG. 1, the apparatus for carrying out the method comprises a filter assembly 12 having a plurality of hollow fiber membranes 14. The terminal ends of the fibers are potted into an extraction header 16 which provides fluid communication between the hollow interior 15 of each of the fiber membranes and into the interior lumens of the triple-lumen catheter 20. The catheter 20 comprises a first lumen 22 for directing backflush fluid through the header 16 into the hollow interior of the elongated fiber membranes. A second lumen 24 directs plasma from the filter assembly to a plasma treatment apparatus 34 to provide ultrafiltration, dialysis, replacement, column adsorption, or a bioreactor or other such apparatus for treating or utilizing the plasma. A third lumen 26 directs the treated plasma back to the patient. Providing a separate lumen (22) for backflush fluid instead of using exudate lumen (24) for backflush eliminates deadspace in lumen 24 and the necessity of removing and reintroducing exudate to accommodate such backflush. The apparatus also includes one or more positive displacement pumps. A first pump 21 pumps fluid from a source of backflush fluid 32 at predetermined intervals and for a predetermined and selected duration as will be explained further hereinafter. A second positive displacement pump 23 pumps plasma exudate from the filter assembly via catheter lumen 24 through the treatment apparatus 34 and back to the patient via third catheter lumen 26. An optional third positive displacement pump 25 may be used to pump the treated plasma or plasma component back to the patient via third catheter lumen 26. The catheter includes an orifice 27 which directs the returned treated plasma into the patient's blood vessel 11. In other embodiments, an apparatus may use one pump for plasma to and from the patient, a second pump for backflush, and a third pump for removing plasma or plasma components to be discarded such as water or for pumping dialysate through a hemofilter.

In the embodiment illustrated in FIG. 1, the apparatus is provided with means for collecting and disposing of plasma components such as toxins, excess plasma water, etc, separated in the plasma exudate in treatment apparatus 34, and not to be returned to the patient. Such means is connected to the plasma treatment apparatus via conduit 37 and includes a collection container 39 and a pump 28 for pumping the effluent to be removed from the plasma exudate to the container. The filter assembly 12, including the header and elongated hollow microporous membrane fibers 14, is implanted in a blood vessel 11 of the patient, preferably the vena cava or other suitable blood vessel, as described in the aforesaid patents.

Figure 3:
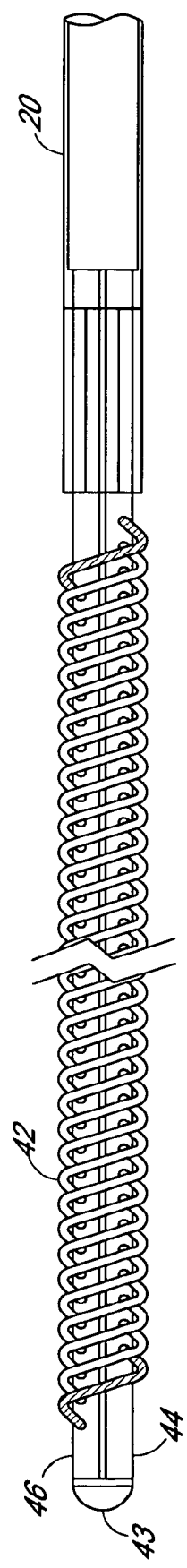
FIG. 3 is a view of a preferred embodiment of a filter device to be implanted in a patient for carrying out in-vivo plasmapheresis.

A preferred filter device to be implanted comprises one or more elongated hollow tubes and a plurality of elongated microporous hollow fibers secured to the one or more tubes. In a preferred embodiment of a filter device illustrated in FIG. 3, a pair of elongated hollow tubes are joined side-by-side lengthwise to form the core of the filter device. The fibers 42 are secured on the hollow tubes such that the interior lumen of each hollow fiber communicates with the hollow interior of the tubes. The two elongated hollow core tubes 44 and 46 terminate at a distal end with a distal end plug or cap 43 formed of a material that seals the open tube ends. The tubes and end cap may be made of any suitable biocompatible material, for example, medical grade urethane. Other biocompatible materials include synthetic rubbers, polycarbonate, polyethylene, polypropylene, nylon, etc. The elongated hollow tubes may be secured together using suitable bonding material 48, adhesive compositions, etc., for example, a UV curable adhesive applied along the length between the two tubes. The length and diameter of the filter device may be selected to accommodate the vessel or vein in which it is to be implanted. Examples of suitable tube lengths for human patients are between about 15 cm and about 25 cm, and preferably between about 18 cm and about 22 cm. Where a pair of core tubes is used as shown in the preferred embodiment, an outer diameter of each tube of between about 1 mm and about 3 mm is suitable. Although two tubes are shown in the filter device, one tube may be used as described and shown in aforesaid application Ser. No. 11/078,016. Such filter devices are further described in U.S. Pat. No. 6,899,692, incorporated by reference herein in its entirety, and in aforesaid application Ser. No. 11/078,016.

Figure 2:
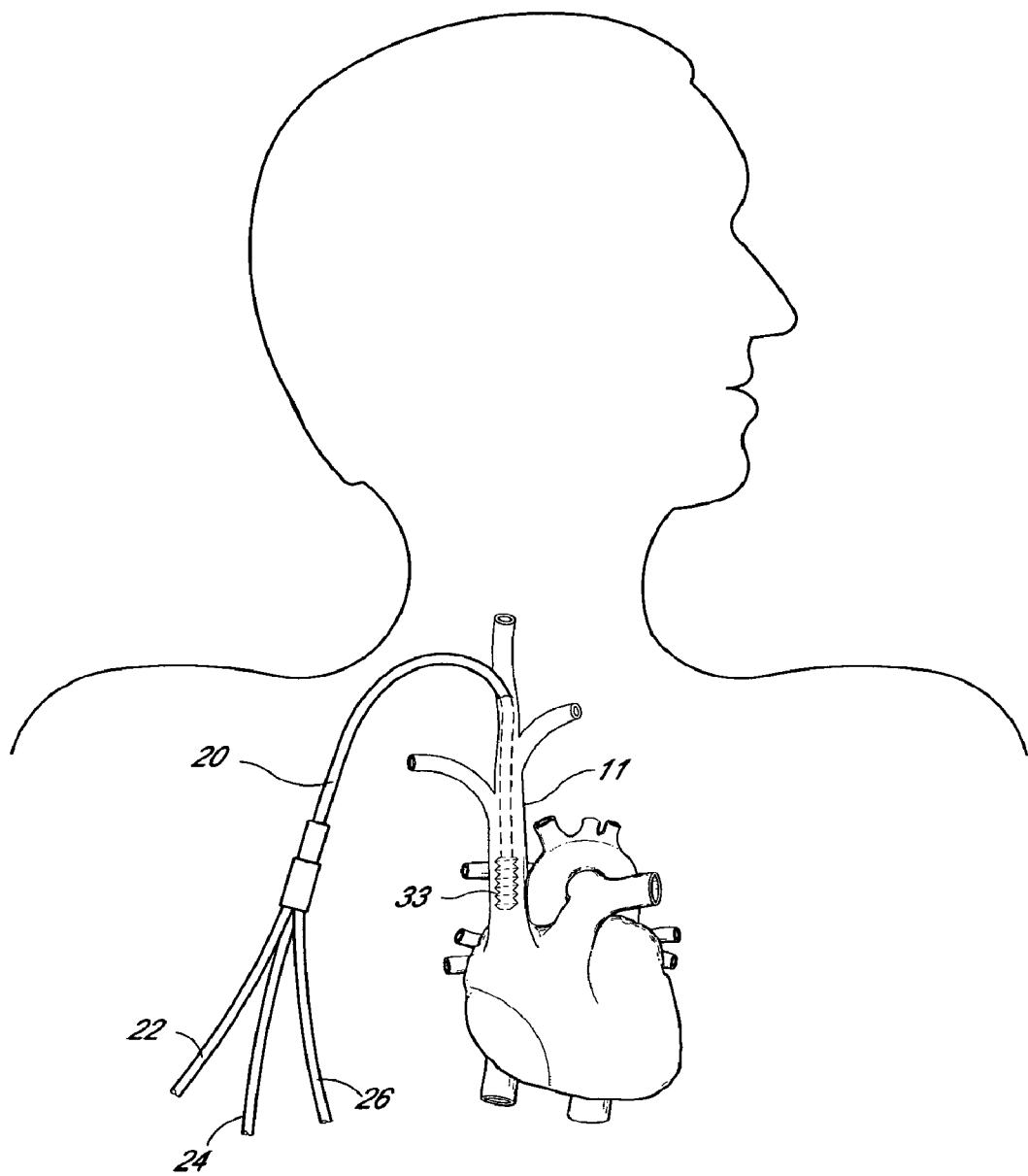
FIG. 2 illustrates an apparatus including a filter and catheter implanted in a patient for carrying out the method.

A preferred fiber membrane used in the filter assembly is disclosed in aforesaid U.S. Pat. No. 6,802,820. The morphology of the fiber walls is asymmetrical between the inner fiber lumen and the outer fiber wall which is in direct contact with the blood flowing in the vasculature in which the device is implanted. The microporous fiber wall structure is a substantially continuous change in mass density as the pore size changes between the fiber walls and comprises a continuum of voids bounded by solid frames as shown in the aforesaid patent. Such a membrane may be described as a plurality of mass density zones between the inner and outer wall surfaces, each zone having a different mass density than the mass density of an adjacent zone. The membrane fiber wall may have two, three or four or more mass density zones with a lower mass density zone at the inner wall surface and a higher mass density zone at the outer wall surface. Each zone is characterized by a different average nominal pore size, with a lower mass density zone having a nominal average pore size of between about 1 um and about 60 um and a higher mass density zone having a nominal average pore diameter of between about 0.3 um and about 1 um. A preferred membrane has the capability of extracting up to 0.75 (ml/min)/(cm$^2$× mm Hg) at transmembrane pressures of between about 5 mm and about 50 mmHg. An implanted filter assembly is illustrated in FIG. 2 and further described in the aforesaid patents.

Referring to FIG. 1, the backflush fluid source 32 comprises a container, bag or other suitable source of a backflush fluid, for example, a normal saline solution, or a source of normal fresh or fresh frozen or treated autologous plasma from which toxins, high molecular weight proteins and/or other undesirable contaminants have been removed. The backflush fluid also contains an anticoagulant and/or other desirable components as described hereinafter. The apparatus includes a microprocessor/controller 38 which controls operation of the pumps and manages the system. The microprocessor/controller is calibrated to determine the flowrate of the pumps. The system may include one or more pressure transducers for monitoring the pressure of fluids within all lumens. Such transducers, not shown, may be used to measure the transmembrane pressure thereby indicating when the pores of the filter have become clogged to an extent to terminate the extraction period, and initiate the backflush operation of the apparatus. Depending on the exudate flow determined by the microprocessor/controller and the transmembrane pressure sensed by such transducers, the microprocessor/controller may determine the duration of the backflush period, as well as the backflush flow rate to be used for substantially cleansing the pores of the fiber membrane. Pumps may also be provided having variable pressure capabilities which may also be regulated by the microprocessor/controller, if desired. The microprocessor/controller 38 may be used to manage the system through monitoring of the flows in the lumens of the catheter, particularly the flow of the exudate through catheter 24 and the pumping of the backflush fluid through the catheter lumen 22. Pump 25 may also be operated by the microprocessor/controller for returning the desired amount of treated plasma to the patient.

The backflush cycle is periodic and preferably provided at a high trans-membrane pressure and low volume, i.e., a low multiple of the volume contained in the membrane lumens of the hollow fibers of the filter and the extraction header. The combination of high pressure and relatively short injection times for backflushing clears the pores and dislodges adhered proteins, thereby restoring pore integrity and density of the virtual filter area to maintain or improve performance level after each backflush cycle. Thus, the process of the invention not only prevents degradation due to clogging, but over time improves the yield of trans-membrane exudate flux in terms of (ml/min)/(cm$^2$× mm Hg) by progressively adjusting and thus optimizing the backflush parameters. Backflush pressures used are between about 100 and about 450 mm Hg which are substantially less than the trans-membrane pressure which is deemed safe since the burst pressures of the membranes are greater than 760 mm Hg.

As previously noted, the pumps used in the apparatus are positive displacement roller pumps. Thus, the fluid flows for both exudate extraction via catheter lumen 24 and backflush fluid injection via catheter lumen 22 are functions of the diameter of the tubing used and the pump revolutions per second. The microprocessor/controller is calibrated to the parameters of the tubing diameter and pump revolutions, thereby equating fluid volume pumped to the time of operation. For example, the setting of the parameters for the control and regulation of the pumps may be empirically determined for equating the volume and time for exudate extraction and backflush injection functions of the apparatus. Such parameters found to be useful for plasmapheresis have been empirically determined for an exudate extraction period of between about 240 and about 600 sec, and a backflush duration of between about 5 and about 50 sec, thereby yielding a preferred backflush fluid flow of between 5 and 50 ml/min. For example, a preferred backflush duration is 5 sec with a flow rate of 30 ml/min. The settings for such parameters are determined by catheter design and by blood flow conditions around the filter and plasma extraction membrane. Again, it is desired and preferred to deliver a minimum amount of saline backflush fluid for cleansing the hollow fiber membrane pores. Moreover, the volume of the backflush injection bolus must be greater than the dead space volume of the catheter extraction header, the inner lumen of the hollow fibers, and the interstitial space in the membrane walls. In addition to the dead space volume, a certain amount of saline is needed to wash out the material that fouls the membrane. The volume of this washing fluid is dependent upon the surface area of the membrane and may be expressed as a bolus flux in $ml/cm^2$. By way of example, a bolus flux used for either in-vivo or in-vitro pre-clinical studies, was between 0.03 $ml/cm^2$ and 0.2 $ml/cm^2$. Again, the injection bolus volume is determined from the dead space volume and the membrane surface areas set by the catheter design.

The time between backflush periods may be determined by how quickly the membrane becomes clogged. Unnecessarily short intervals between backflushes results in higher average backflush volumes, thereby reducing the amount of plasma removed. On the other hand, where backflush intervals are overly long, plasma flow rates decline due to filter fouling. For example, an empirically determined interval between backflushes of 300 sec has been found to be useful for existing catheter designs.

The flow rate for backflush fluid injections is determined by pressure limitations of the catheter, the effect of flow velocity for substantially cleansing or clearing the membrane, and the amount of backflush or bolus volume required. A rise in pressure is a result of resistance to flow due to clogged membranes and is a function of the backflush flow rate, membrane surface area, and level of membrane clogging. The flow rate is also limited by the amount of pressure that the inner lumen of the catheter and fibers can withstand without failure. As previously noted, the velocity or pressure of the backflush fluid must be sufficient to dislodge the clogging material in all of the membrane surface. The duration of the backflush bolus may also be lengthened or shortened to adjust the backflush flow volume. While the period between backflush intervals and the flow rate are closely related to membrane clearing requirements, the duration is not, thereby making it an obvious choice for adjustment of bolus volume. For example, a catheter with a dead volume of 2.0 ml and a surface area of 40 $cm^2$ requires a bolus volume of 2.5 ml. A plasma extraction period of 300 sec and a backflush flow rate of 30 ml/min results in a backflush duration of about 5 sec.

The clogging or fouling of the filtration membrane is a function of the flow rate of exudate through the extraction filter assembly, the size of which, i.e., $cm^2$ of membrane surface area, is dictated by the clinical application to be served. Generally, the more advanced disease state of organ failure to be served requires greater exudate flow rate and a greater membrane surface area, resulting in earlier degradation of extraction performance and requiring a more aggressive program for backflush cleansing of the membrane. Thus, for example, treatment of advanced acute renal failure (ARF) and end stage renal disease (ESRD) requires substantially higher fluid extraction rates for optimum clinical results as compared to fluid management systems for treating congestive heart failure (CHF).

Figure 4:
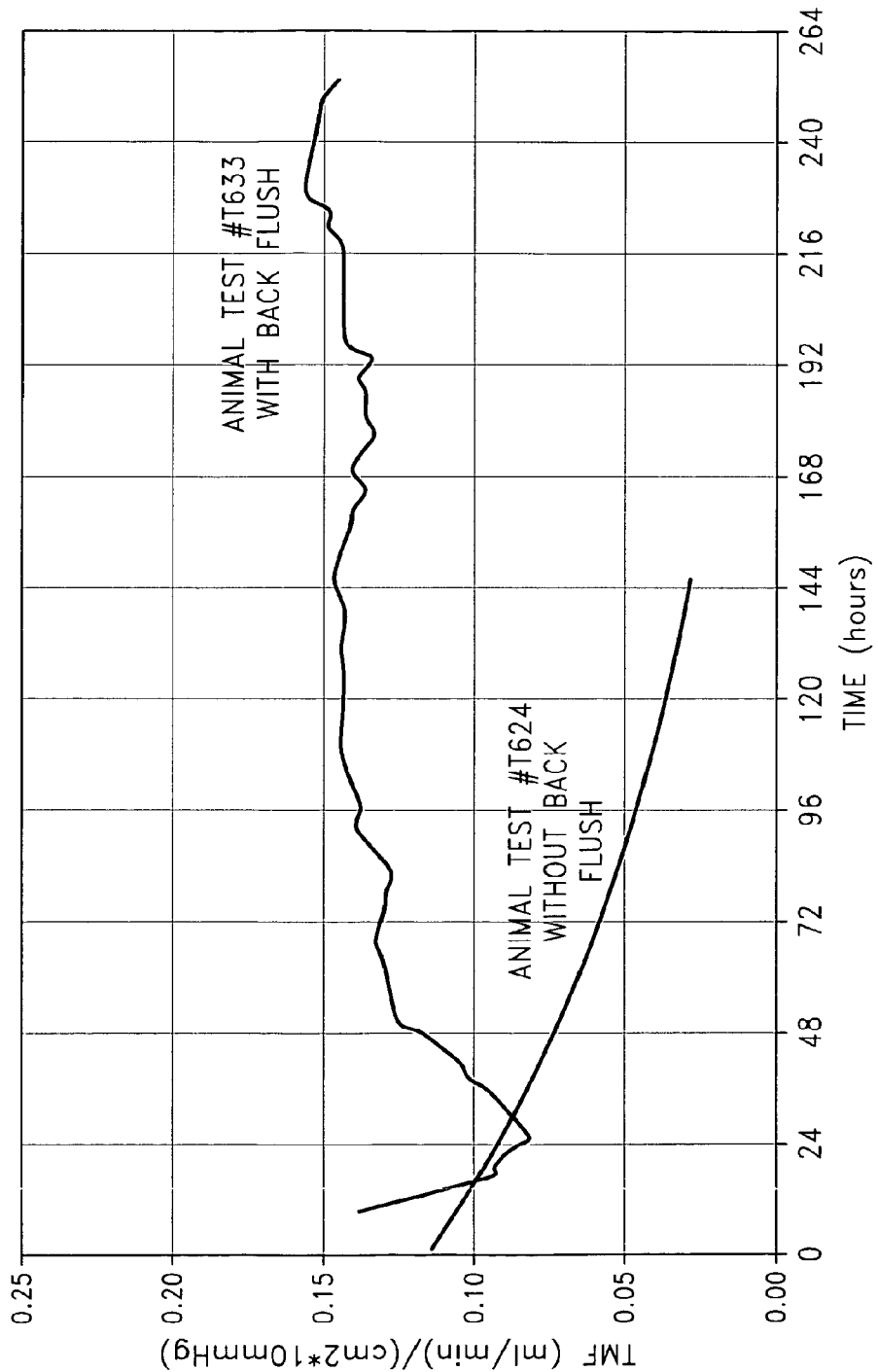
FIG. 4 is a graph illustrating trans-membrane flux degradation trends with and without periodic backflush according to the method.

A comparison of a system using backflush components and methods with a system having no backflush is illustrated in the graph of FIG. 4, and based on actual test results which have been repeated over time. The results show marked improvement using apparatus and method described herein.

Useful backflush fluid may be a normal saline containing other desirable components. In one embodiment, the backflush fluid incorporates an anticoagulant or antithrombosis agent to provide systemic anticoagulation, or to provide localized anticoagulation protection to the fibers for reducing or inhibiting thrombosis or clotting at or near the fiber surface and within the fiber wall itself. Some very useful fiber polymers will not have anticoagulant component retaining sites, while other useful polymers may include antithrombosis activity, for example, polymers with heparin, citrate or NO donor receptors. Where such antithrombotic properties are not permanent, for example, where the anticoagulant component is not permanently bound to the polymer, backflushing with heparin, citrate or NO donor containing fluid will replenish the membrane with anticoagulant for continued thromboresistance throughout the in-vivo plasmapheresis. Desired and useful concentrations of heparin, citrate or NO donors or other pharmaceutical anticoagulants (such as coumadin, warfarin, etc.) in the backflush fluid may be determined by those skilled in the art. For example, useful amounts of heparin in a backflush fluid such as a normal saline solution for sustaining the thromboresistance of fibers are of at least 1 IU and preferably 2 IU or more per kilogram of human patient body weight for backflushing at 5 minute intervals, the specific amount being sufficient for local anticoagulation but insufficient to provide systemic anticoagulation. For treating the fibers for continuing thromboresistance, heparin concentrations of between about 25 IU and 300 IU per ml and preferably between about 75 IU and about 150 IU per ml of backflush fluid may be used. The backflush fluid may also be used to induce systemic anticoagulation. For example, a single backflush 2.5 ml bolus containing between about 25 IU and about 150 IU heparin and preferably between about 50 IU and about 100 IU heparin per kilogram of human patient body weight should be sufficient to induce systemic anticoagulation. Moreover, systemic anticoagulation may be maintained using heparin backflush concentrations somewhere between the aforesaid fiber treatment and systemic inducement concentrations. However, other concentrations of heparin may be used or adjusted where desired or as determined or prescribed, depending on current anticoagulation therapy of the patient backflush intervals, duration, and other process and backflushing variables such as described herein. The heparin may be conventional unfractionated heparin or low molecular weight (fractionated) heparin (LMWH).

Where the use of heparin is contraindicated, other anticoagulants/antithrombotic agents may be used. A useful anticoagulant is a citrate, which may be provided in any suitable form including citric acid and citrate salts such as alkali or alkaline earth metal salts, e.g. trisodium citrate. Again, it may be desirable to use citrate concentrations sufficient for local anticoagulant but insufficient for systemic anticoagulation. Useful amounts of sodium citrate (trisodium citrate) in the backflush fluid in a normal saline solution are at least 0.1 mol/liter, preferably greater than about 0.2 mol/liter, e.g. about 0.3 mol/liter to about 1.0 mol/liter. For example, 0.5 mol/liter sodium citrate delivered at a rate of about 10 mmol/hour may be suitable to induce systemic anticoagulation. Other concentrations of sodium citrate may be used depending on backflush intervals, duration and other process variables. Protons or and/or metal cations may also be provided such as described in U.S. Pat. application publication (U.S. Pat. No.2005/0119598), incorporated herein by reference. Calcium chloride may be used in the sodium citrate backflush fluid to provide desirable ionized calcium concentration such as described in *Kidney International*, vol. 56, (1999), pp. 1578-1583. Other anticoagulants may be used in the backflush, for example, warfarin, acenocoumarol, phenindione, prostacyclin, 1, 3-indanedines, bivalirudin and others known to these skilled in the art.

Nitric oxide or NO donors may also be used to provide anticoagulance and thromboresistance. A number of useful nitric oxide donors and their nitric oxide release reactions and applications are reported by Wang, et al. in *Chemical Reviews*, 2002, vol. 102, No. 4, pp. 1091-1134. Specific examples of such NO donors include organic nitrates, organic nitrites, N-nitrosimines, nitrosothiols(RSNOs), sydnonimines, C-nitroso compounds, furoxans and benzofuroxans, oxatriazale-5-imines, oximines, N-hydroxyguanidines, and diazeniumdiolates as well as others disclosed in the article and known to those skilled in the art. Desired and useful concentrations of such NO donors used in the backflush fluid will be determined by those skilled in the art. Other compositions that may be used in the backflush are those capable of generating nitric oxide production, for example, catalysts capable of reducing endogenous NO donors such as nitrites, nitrates or nitrosothiols. Exemplary catalysts include enzymes such as mammalian xanthine oxidase or biomimetic catalysts such as copper (II)-ligand complexes that convert nitrite, nitrate or nitrosothiols to NO. Such catalysts are described in U.S. Patent Application Publication Nos. 2002/0115559 and 2004/0224868, both of which are incorporated herein by reference.

Yet other anticoagulant/thromboresistant compositions for treating the fiber membranes are fibrin or thrombin reducing enzymes. For example, small amounts of one or more of such enzymes may be added to the backflush. Examples of such enzymes include proteolyic enzymes, aprotinin, and others known to those skilled in the art.

Patient medications may also be administered via the backflush fluid. Any number of such medications, for example, antihistamines, antidepressants, antihypertensives, antibiotics, statins, ACE inhibitors, beta blockers, calcium channel blockers, analgesics and the like may be incorporated in the backflush fluid and directed through the fiber walls into the patient's bloodstream during a backflush cycle, or as an adjunct procedure using the backflush fluid and procedure, with or without an anticoagulant or antithrombotic agent. Thus, such medications may be administered within the normal or prescribed backflush cycle or at other times, cycles and/or using fluid volumes, pressures and durations independent from those used in the typical backflush for clearing and cleansing the fiber pores.

Medical applications of systems using the aforesaid methods include fluid management such as described in U.S. Pat. application Ser. No. 11/078,016 filed Mar. 11, 2005 (TRANSVI.011CP1) for patients in decompensated congestive heart failure and prevention of pre-renal kidney failure and acute respiratory distress syndrome, treatment of refractive congestive heart failure and acute renal failure, for therapeutic apheresis systems such as described in U.S. Pat. No. 6,849,183, for immune system disease and blood component therapy, edema, management systems for ascites, lymphedema, and selective systemic edema, post surgical and traumatic edema, tissue engineering applications including bioreactors and hybrid bio-organs, and dialysis systems for end stage renal disease. Other uses and applications will be appreciated by those skilled in the art.

What is claimed is:

1. A method for carrying out plasmapheresis, comprising: providing a filter device comprising a plurality of elongated hollow microporous fibers;
diffusing plasma and toxins from a patient's blood through the wall of the fibers into the hollow interior thereof; and
periodically interrupting the diffusion of plasma and toxins and backflushing the fibers by directing a backflush fluid containing an amount of anticoagulant at least sufficient to provide fiber thromboresistance through a catheter into the fibers at a pressure and for an interval sufficient to substantially clear the pores of the filter, and after the interval, resuming the diffusion of plasma.

2. The method of claim 1, comprising using a backflush fluid comprising a saline solution containing heparin.

3. The method of claim 2, wherein the NO donor is in a concentration sufficient to provide local anticoagulation and insufficient to provide systemic anticoagulation.

4. The method of claim 2, wherein the NO donor comprises at least one member selected from the group consisting of a N-nitrosimine, nitrosothiol, organic nitrate, organic nitrite, oximine, sydnonimine, C-nitroso compound, furoxan, benzofuroxan, N-hydroxyguanidine, and diazeniumdiolate.

5. The method of claim 1, comprising backflushing at a pressure of between about 15 and about 100 mg Hg for an interval of between about 5 and about 50 seconds.

6. The method of claim 1, for inducing systemic anticoagulation comprising using a single bolus of backflush fluid containing heparin.

7. The method of claim 1, for maintaining systemic anticoagulation comprising using a backflush fluid containing more than about 150 IU heparin per ml.

8. The method of claim 1, wherein toxin-containing plasma from the fibers is directed to plasma treatment apparatus through a second lumen of the catheter.

9. The method of claim 8, wherein plasma from plasma treatment apparatus is directed to a third lumen of the catheter and returned to the patient.

10. The method of claim 1, wherein the anticoagulant comprises sodium citrate.

11. The method of claim 10, comprising using a backflush fluid comprising a saline solution having a sodium citrate concentration of at least 0.1 mol/liter.

12. The method of claim 11, wherein the sodium citrate concentration is sufficient to provide local anticoagulation and insufficient to provide systemic anticoagulation in a human patient.

13. The method of claim 11, wherein the sodium citrate concentration is sufficient to provide systemic anticoagulation in a human patient.

14. The method of claim 1, wherein the anticoagulant comprises a NO donor.

15. The method of claim 1, wherein the backflush fluid contains patient medication.

16. A method for carrying out plasmapheresis, comprising:
providing a filter device, the filter device comprising one or more elongated hollow tubes and a plurality of elongated microporous fibers capable of separating plasma from whole blood, each fiber having an interior lumen extending along the length thereof and having a first and second end secured to one or more of the elongated hollow tubes wherein the interior lumen of each of the fibers communicates with the interior of the one or more hollow tubes;
providing a catheter in fluid communication with the hollow interior of the fibers, and diffusing plasma and toxins from a patient's blood through the wall of the fibers into the hollow interior thereof; and
periodically interrupting the diffusion of plasma and toxins and backflushing the fibers by directing a backflush fluid containing an amount of anticoagulant at least sufficient to provide fiber thromboresistance through the catheter into the fibers at a pressure and for an interval sufficient to substantially clear the pores of the filter, and after the interval, resuming the diffusion of plasma.

17. The method of claim 16, wherein the anticoagulant comprises at least one member selected from the group consisting of heparin, citrate, and a NO donor.

18. The method of claim 17, wherein a concentration of the anticoagulant is sufficient to provide local anticoagulation.

19. The method of claim 18, wherein a concentration of the anticoagulant is insufficient to provide systemic anticoagulation in a human patient.

20. A method for carrying out plasmapheresis comprising:
providing a filter device, the filter device comprising one or more elongated hollow tubes and a plurality of elongated microporous fibers having an interior lumen extending along the length thereof, each fiber having a first and second end secured to the one or more elongated hollow tubes, wherein the interior lumen of each of the fibers communicates with the interior of the one or more hollow tubes, and wherein each of the elongated microporous fibers have an asymmetrical fiber wall morphology between the inner wall surface extending along the interior fiber lumen and the outer wall surface, the fiber wall having a higher mass density zone adjacent to the outer wall surface and a lower mass density zone adjacent to the inner wall surface, the higher mass density zone having a smaller average nominal pore size than the average nominal pore size in the lower mass density zone and wherein the fibers are configured to separate plasma from whole blood by passing plasma through the fiber wall from the outer wall surface to the inner wall surface and to the interior lumen thereof;
providing a catheter in fluid communication with the hollow interior of the fibers, and diffusing plasma and toxins from a patient's blood through the wall of the fibers into the hollow interior thereof; and
periodically interrupting the diffusion of plasma and toxins and backflushing the fibers by directing a backflush fluid containing an amount of anticoagulant at least sufficient to provide fiber thromboresistance through the catheter into the fibers at a pressure and for an interval sufficient to substantially clear the pores of the filter, and after the interval, resuming the diffusion of plasma.

21. The method of claim 20, wherein the anticoagulant comprises at least one member selected from the group consisting of heparin, citrate, and a NO donor.

22. The method of claim 21, wherein a concentration of the anticoagulant is sufficient to provide local anticoagulation.

23. The method of claim 21, wherein a concentration of the anticoagulant is insufficient to provide systemic anticoagulation in a human patient.

* * * * *